US008591551B2

(12) United States Patent
Miller

(10) Patent No.: US 8,591,551 B2
(45) Date of Patent: Nov. 26, 2013

(54) LINKED SPINAL STABILIZATION ELEMENTS FOR SPINAL FIXATION

(75) Inventor: Keith E Miller, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 294 days.

(21) Appl. No.: 13/006,889

(22) Filed: Jan. 14, 2011

(65) Prior Publication Data

US 2012/0184995 A1 Jul. 19, 2012

(51) Int. Cl.
*A61B 17/70* (2006.01)
(52) U.S. Cl.
USPC ........................................................ 606/264
(58) Field of Classification Search
USPC ......... 606/246, 256, 260, 261, 262, 264–267, 606/270, 277, 278, 280, 70, 71, 283, 286, 606/287, 301, 305, 308
See application file for complete search history.

(56) References Cited

U.S. PATENT DOCUMENTS

| 3,858,578 | A | * | 1/1975 | Milo ............................. 600/229 |
| 6,296,644 | B1 | | 10/2001 | Saurat et al. |
| 7,223,290 | B2 | | 5/2007 | Errico et al. |
| 7,628,816 | B2 | * | 12/2009 | Magerl et al. .............. 623/17.16 |

FOREIGN PATENT DOCUMENTS

WO      WO 0106939 A1 *  2/2001

* cited by examiner

*Primary Examiner* — Pedro Philogene
*Assistant Examiner* — David Comstock

(57) ABSTRACT

Apparatus, methods, systems, procedures and implants for linking two or more anchors engaged to two or more vertebrae of a spinal column are provided. The systems include a plate assembly to stabilize one or more vertebral levels with first and second plate segments pivotally coupled to one another between anchors engaged to respective vertebrae of the vertebral level. The plate segments are manipulated to secure the plate segments to the respective vertebrae and lock the plate segments in position relative to one another.

18 Claims, 7 Drawing Sheets

LINKED SPINAL STABILIZATION ELEMENTS FOR SPINAL FIXATION

BACKGROUND

The invention relates generally to medical devices and procedures. More particularly, the invention relates to apparatus and methods for stabilization of one or more vertebral levels in, for example posterior procedures, or in procedures at other locations associated with the spine.

Stabilization of one or more levels of the spine is often accomplished with placement of a rod construct or plate between bone anchors engaged to the vertebrae of the one or more levels. These procedures may also involve placement of a second rod construct or plate on the contra-lateral side of the vertebrae, and securing the bi-laterally positioned devices with a cross-connector. The procedures employing rods may also involve reduction of one or more the vertebrae in order to position the rod in anchor engaged to the vertebrae and to align the vertebrae in a desired position, and bending or contouring of the rod to fit the anchor locations along the vertebrae. These systems require in situ application of forces to the anchors and/or the spinal rod to bend the rod, and can be time-consuming and involve complicated surgical instruments and maneuvers to assist in applying the desired forces and in fitting the rod to the anchors. The procedures employing plates can be limited in that bending of the plate is possible only in one plane where the thickness of the plate allows such bending, while lateral bending of the plate is not possible or extremely difficult to accomplish during surgery due to the width of the plate being greater than its thickness.

Thus, a need exists for improved spinal stabilization systems and procedures for insertion and securement of implants at locations within a patient's body that can simplify the procedures and minimize intrusion and invasiveness into tissue of the patient, reducing post-operative pain and healing time for the patient.

SUMMARY

Apparatus, methods, systems, procedures and implants for linking two or more anchors engaged to two or more vertebrae of a spinal column are provided. The systems include a plate assembly to stabilize one or more vertebral levels with first and second plate segments pivotally coupled to one another between anchors engaged to respective vertebrae of the vertebral level. The plate segments are manipulated to secure the plate segments to the respective vertebrae and lock the plate segments in position relative to one another. In one form, at least one of the plate segments includes at least two components that are compressed, flexed, squeezed, deformed, bent, or otherwise manipulated relative to one another to lock it to an adjacent plate segment. In one refinement, each plate segment of the plating system can be manipulated to lock it to the adjacent segment. In a further refinement, at least one plate segment includes a socket that receives a ball member that extends from the adjacent plate segment to pivotally couple the plate segments to one another. The socket sizes can be reduced by manipulating the anchor to which the plate segment is engaged to lock the adjacent plate segments in position relative to one another.

According to one aspect, a spinal stabilization system comprises at least a first anchor engageable to a first vertebra and a second anchor engageable to a second vertebra. The first and second anchors each include a bone engaging portion and a mounting portion extending proximally from the bone engaging portion. Each of the first and second anchors further includes an engaging member. The system also includes a first plate segment with a first body defining a first hole extending therethrough for receiving the first anchor and a socket, and a second plate segment with a second body defining a second hole extending therethrough for receiving the second anchor. The second body of the second plate segment includes a member extending into the socket to pivotally connect the second plate segment to the first plate segment. The engaging member of the first anchor is movable to manipulate the first body of the first plate segment to collapse the socket around the member and lock the second plate segment in position relative to the first plate segment.

According to another aspect, a spinal stabilization system comprises at least a first anchor engageable to a first vertebra and a second anchor engageable to a second vertebra, with the first and second anchors each including a bone engaging portion and a mounting portion extending proximally from the bone engaging portion. Each of the first and second anchors further includes an engaging member engageable to its mounting portion. The system also includes a first plate segment with a first body defining a first hole extending therethrough for receiving the first anchor. The first body includes first and second components that flex relative to one another and that each define a respective portion of a socket. The system also includes a second plate segment with a second body defining a second hole extending therethrough for receiving the second anchor. The second body of the second plate segment includes a member extending into the socket to pivotally connect the second plate segment to the first plate segment. The engaging member of the first anchor is movable to contact the first body of the first plate segment and flex the first and second components to clamp the portions of the socket against the member extending from the second body to lock the second plate segment in position relative to the first plate segment.

These and other aspects are discussed further below.

DETAILED DESCRIPTION

Figure 1:
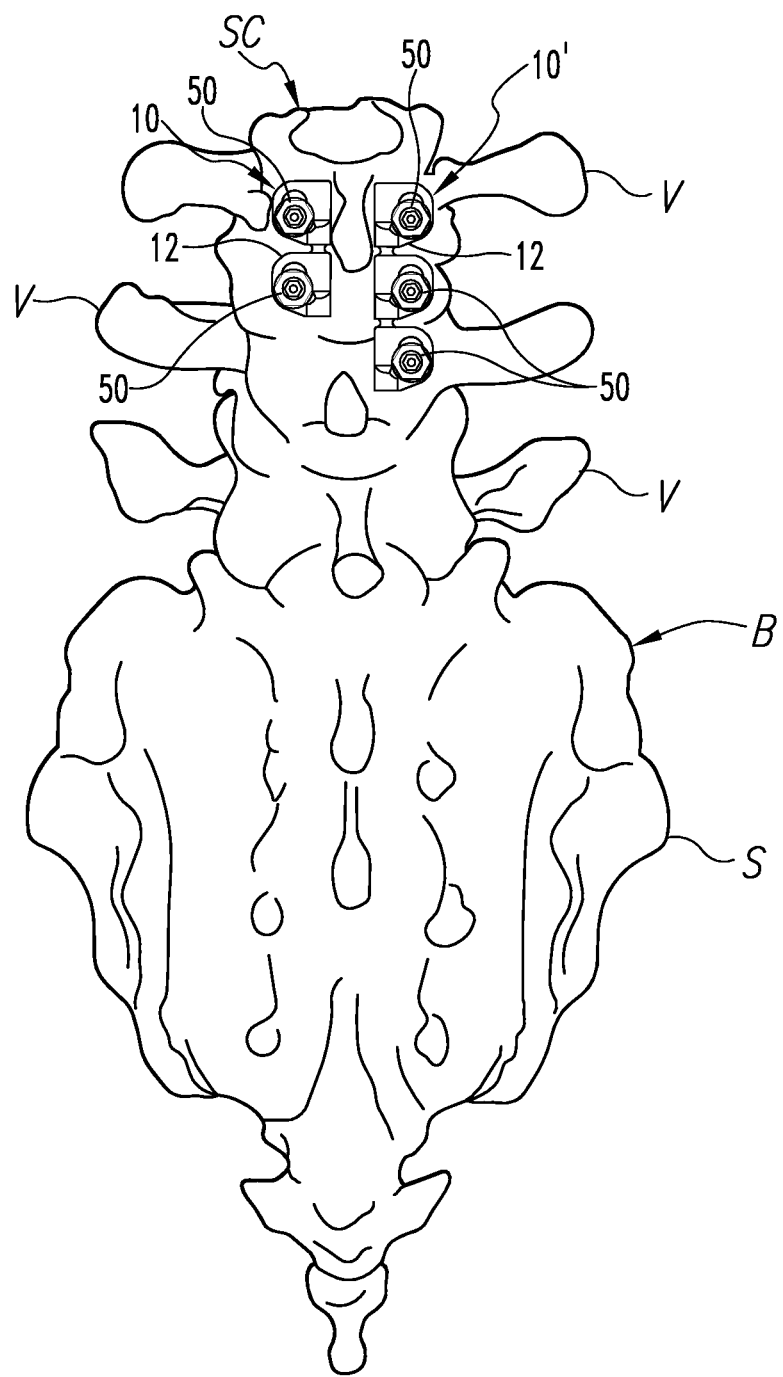
FIG. 1 is an elevation view of a posterior portion of a spinal column including a spinal stabilization system engaged thereto.
Figure 3:
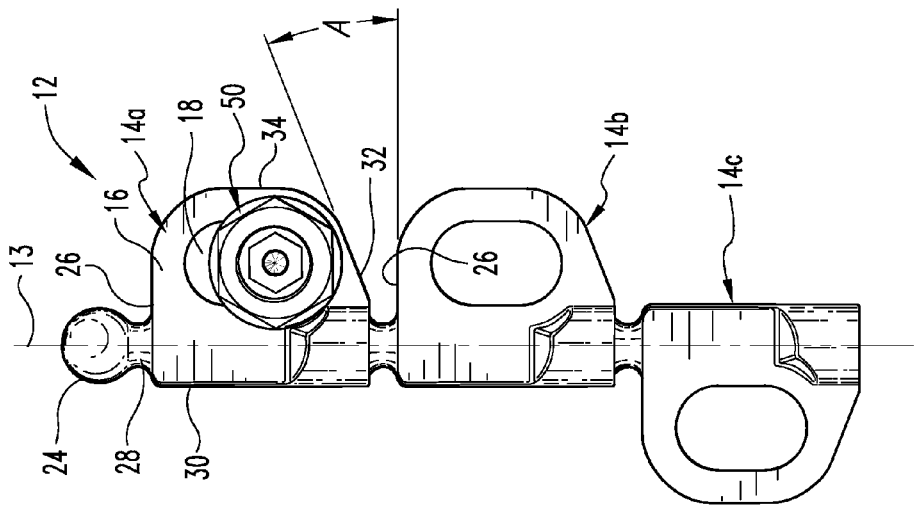
FIG. 3 is a plan view of the spinal stabilization system of FIG. 2.
Figure 2:
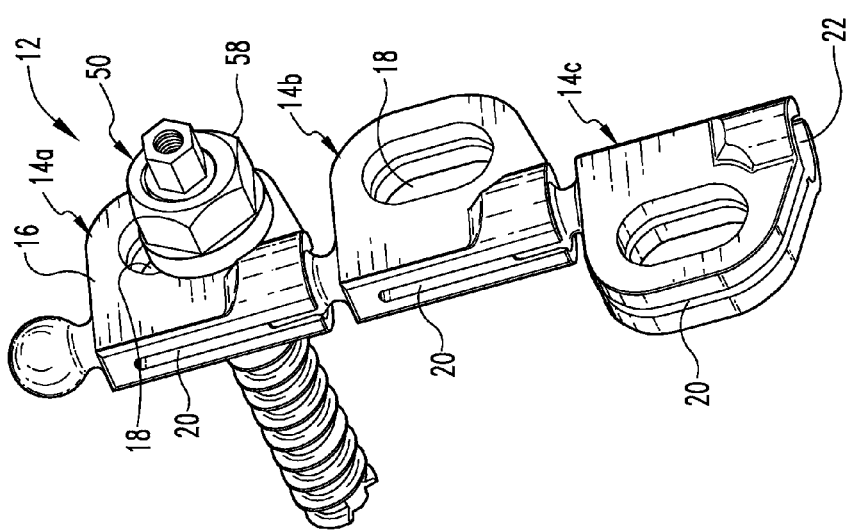
FIG. 2 is a perspective view of one embodiment of the spinal stabilization system.
Figure 4:
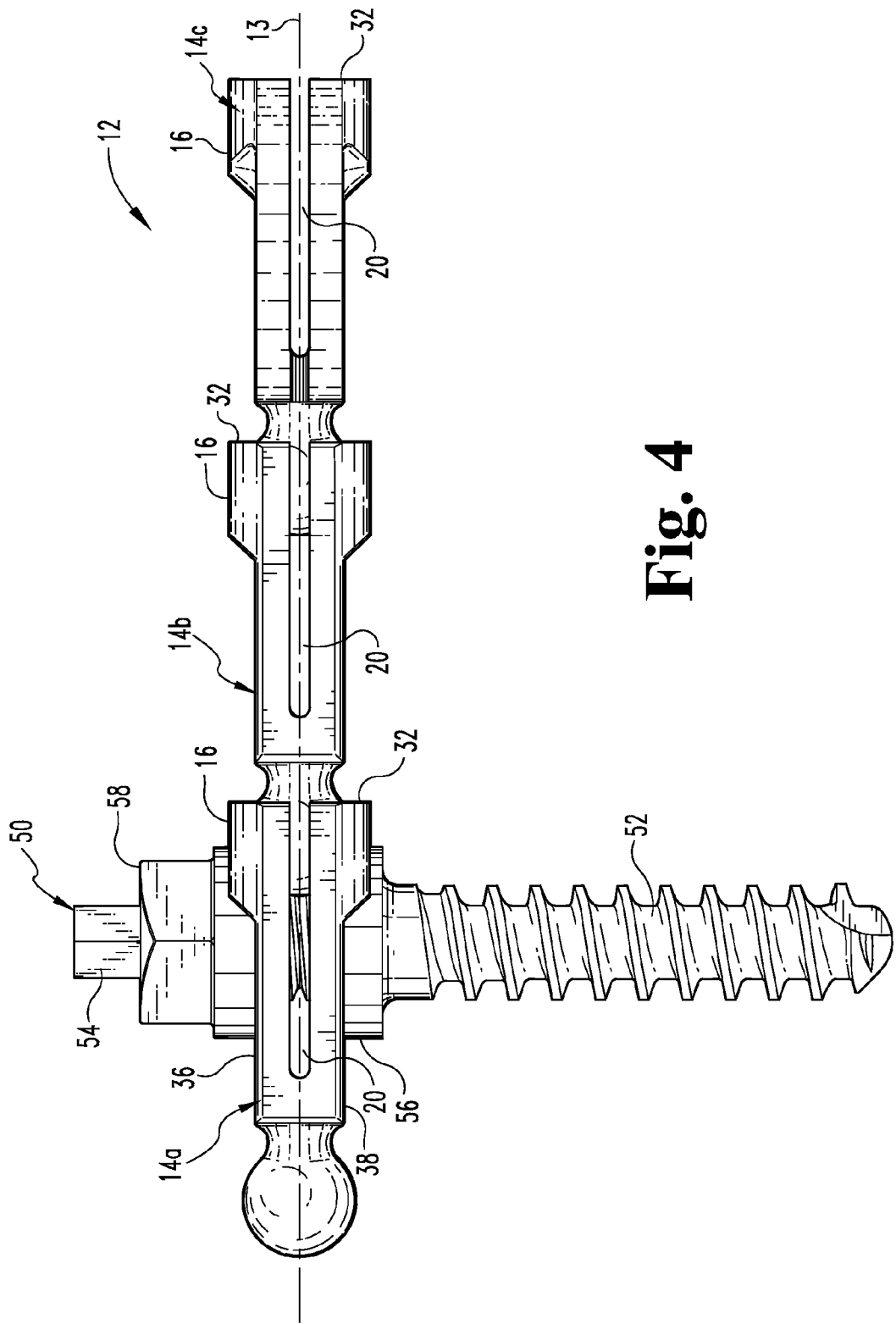
FIG. 4 is an elevation view of the spinal stabilization system of FIG. 2.
Figure 6:
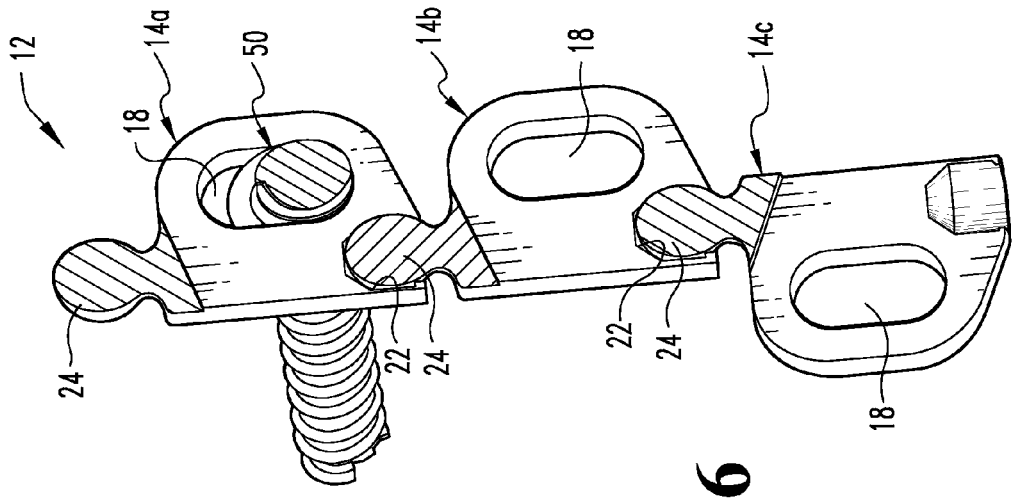
FIG. 6 is a perspective view in longitudinal section of the spinal stabilization system of FIG. 2.
Figure 5:
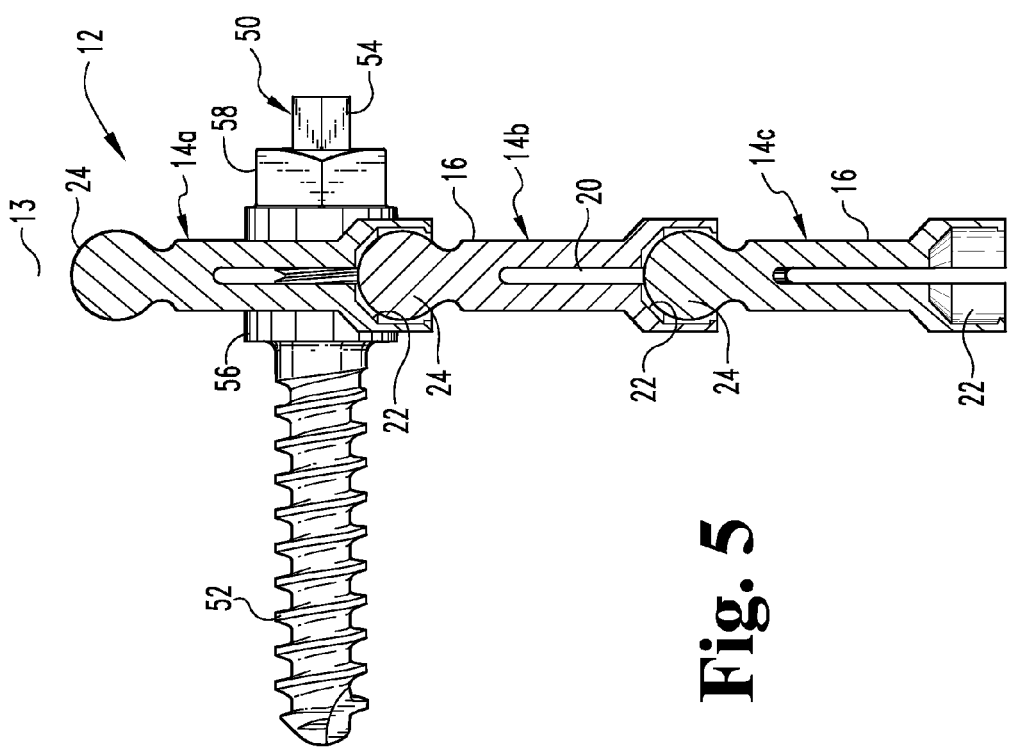
FIG. 5 is an elevation view in longitudinal section view of the spinal stabilization system of FIG. 2.

For the purposes of promoting an understanding of the principles of the invention, reference will now be made to the embodiments illustrated in the drawings and specific language will be used to describe the same. It will nevertheless be understood that no limitation on the scope of the invention is intended. Any alterations and further modifications in the illustrated devices and described methods and further applications of the principles of the invention as disclosed herein are contemplated as would normally occur to one skilled in the art to which the invention relates.

Apparatus and methods disclosed herein include spinal stabilization systems implantable into the body of a patient for stabilization along, for example, two or more vertebrae of a spinal column. The stabilization systems include at least one plate assembly engaged to at least two vertebrae with bone anchors to provide a stabilization effect to at least one motion segment of the spinal column. The plate assembly includes at least first and second plate segments pivotally coupled to one another between the bone anchors at about mid-length of the plate assembly. At least one of the plate segments is manipulated to rigidly fix or semi-rigidly fix it in position relative to the other plate segment. In one refinement, the plate assembly includes three or more plate segments that are pivotally coupled to one another and each plate segment is engaged to a respective vertebra with a corresponding bone anchor. The plates segments are manipulated to lock the plate segments to one another to provide a rigid or semi-rigid plate assembly when secured to the bone anchors. The initial pivotal relationship between the plate segments allows the plate assembly to be adjusted to fit the anchor locations along the spinal column without regard to a specific orientation of the anchors or specific positioning of the anchor mounting locations for the plate segments relative to one another. Once each plate segment is positioned at the desired mounting location along its respective anchor, the plate segments can be manipulated to secure the plate segments in position relative to one another to provide a plate assembly contoured to fit the anchor mounting locations in the patient. This eliminates or reduces the need to bend the plate assembly to fit the anchor locations and the spinal geometry, which simplifies the procedure and allows the plate assembly to be employed even in situations where the anchors are offset laterally relative to one another.

In one embodiment, the plate segments are pivoted toward or away from the spinal column to adjust the plate assembly for anchor mounting locations positioned at different heights of the vertebral bodies. In a further embodiment, the plate segments are pivoted laterally relative to one another to adjust the plate assembly to fit anchor mounting locations that are laterally offset relative to one another and laterally offset from an axis extending parallel to the central axis of the spinal column. In additional embodiments, the plate segments are pivoted to adjust the plate assembly to fit anchor mounting locations that are positioned at different heights from the vertebral bodies of the spinal column and at locations laterally offset from one another. In addition, the plate segments of the plate assembly can be pivoted relative to one another to be positioned along anchors that extend in non-parallel relation to one another.

FIG. 1 illustrates a posterior spinal stabilization system 10 located along a spinal column of a patient. More specifically, stabilization system 10 can be affixed to bones B of the spinal column segment SC from a posterior approach, although applications in posterior-lateral, lateral, antero-lateral and anterior approaches are also contemplated. Bones B can include the sacrum S and several vertebral bodies V. Stabilization system 10 generally includes several bone anchor assemblies 50 and a plate assembly 12 structured to selectively interconnect with bone anchor assemblies 50. Plate assembly 12 may have a length sized to extend between bone anchor assemblies 50 engaged to least two vertebral bodies V positioned adjacent to one another as shown in FIG. 1. The stabilization system 10 spans one or more vertebral levels, and stabilization system 10 is engaged to the vertebrae of the one or more vertebral levels. Other embodiments contemplate plate assembly 12 has a length sized to extend along three or more vertebrae, such as shown with respect to stabilization system 10'. In stabilization systems 10 and 10', bone anchor assemblies 50 are affixed to various locations of the spinal column segment SC, such as the pedicles, and are interconnected with one or more plate assemblies 12. The systems 10, 10' can include one or more plate assemblies 12 engaged uni-laterally along the spinal column segment SC, or one or more plate assemblies 12 engaged bi-laterally along the spinal column segment SC. The plate assemblies 12 can be engaged to posterior elements of vertebrae of the spinal column segment SC, or along the anterior, lateral, antero-lateral, or oblique portions of vertebrae of the spinal column segment SC and combinations thereof. It is contemplated that the spinal column segment SC may comprise any one or combination of vertebrae from the cervical, thoracic, lumbar and sacral portions of the spinal column segment SC. The spinal stabilization system 10 may be used for, but is not limited to, treatment of degenerative spondylolisthesis, fracture, dislocation, kyphosis, spinal tumor, and/or a failed previous fusion.

Referring to FIGS. 2-6, there is shown one embodiment of stabilization system 10 that includes plate assembly 12 with multiple plate segments 14a, 14b, 14c and bone anchor assembly 50. Each plate segment 14a, 14b, 14c is shown to be identical to one another, however identity of plate segments 14a, 14b, 14c is not required. Plate segment 14a will be described in detail, it being understood that the description is applicable to the other plate segments when the segments are identical. In addition, while a single bone anchor assembly 50 is shown engaged to plate segment 14a, it should be understood that one or both of the other plate segments can be engaged to a bone anchor assembly 50 such as shown in FIG. 1. Also, plate assemblies are contemplated that include two plate segments, three plate segments, or more than three plate segments. The user can customize the overall length of the plate assembly by selecting a desired number of plate segments to secure together based on the conditions encountered during surgery or as a result of pre-operative planning.

Anchor assemblies 50 each include a distal bone engaging portion 52 and a proximal mounting portion 54 extending proximally from the proximal end of bone engaging portion 52. Anchor assembly 50 also includes a shoulder 56 positioned between bone engaging portion 52 and mounting portion 54. The distal side of plate segment 14a rests against shoulder 56 projecting outwardly from at least mounting portion 54. Anchor assembly 50 also includes an engaging member 58 engaged to mounting portion 54 that is movable along mounting portion 54 against the proximal surface of plate segment 14a. In the illustrated embodiment, bone engaging portion 52 is a threaded bone screw. Other embodiments contemplate other forms for bone engaging portion 52, including threaded and non-threaded forms, such as hooks, clamps, wires, and adhesives, for example. Mounting portion 54 is a threaded cylindrical post that is formed as a single unit with and as an axially aligned extension from bone engaging portion 52, but may also be formed as a separate piece from bone engaging portion 52 and/or be axially offset from or misaligned with bone engaging portion 52. Mounting portion 54 is fixed relative to bone engaging portion 52, but may also be pivotable, rotatable and/or translatable relative to bone engaging portion 52. Mounting portion 54 may include external threads to threadingly engage internal threads of engaging member 58, or include any other suitable configuration for engaging an engaging member. Engaging member 58 is shown as an internally threaded nut, but may also be in the form of a set screw, cap, plug or other device that is used instead of or in combination with a nut to secure the plate segment against shoulder 56.

Plate assembly 12 extends along a longitudinal axis 13 that is centered with the connection of each of the plate segments 14a, 14b, 14c to one another. The plate segments 14a, 14b, 14c each include a body 16 that defines a hole 18 extending through and opening at proximal surface 36 and the opposite distal surface 38. Distal surface 38 faces the bony portions of the spinal column segment SC to which plate assembly 12 is attached. Body 16 includes a first end wall 26 and an opposite second end wall 32. End walls 26, 32 extending between a first side wall 30 and an opposite second end wall 34. Second end wall 32 is angled away from first end wall 26 at angle A of the adjacent plate segment in the direction away from longitudinal axis 13 to provide clearance for pivoting of plate segment 14a toward and away from first end wall 26 of the adjacent plate segment 14b. Second end wall 32 also defines a socket 22 extending into body 16 that opens through second end wall 32 and is centered on longitudinal axis 13. Plate segment 14a includes a ball member 24 at an end of a stem 28 that extends outwardly from end wall 26. Ball member 24 and stem 28 are centered on longitudinal axis 13. Ball member 24 of plate segment 14b is received in socket 22 of plate segment 14a. Additionally, ball member 24 of plate segment 14c is received in socket 22 of plate segment 14b. The ball and socket connections pivotally link the plate segments with one another and allow universal pivoting of the plate segments to fit with their mounting locations against the respective shoulders 56 of anchor assemblies 50 implanted along spinal column segment SC.

As shown in FIGS. 2-6 with respect to plate segment 14c, the plate segments can be rotated so that hole 18 is offset to the opposite of longitudinal axis 13 relative to the holes of one or more of the other plate segments to accommodate situations in which the anchor assemblies 50 are offset from one another. In FIGS. 2-6 the plate segments 14a-14c are shown in a linearly aligned orientation on longitudinal axis 13. In addition, the plate segments can be pivoted so that one or more of the plate segments is angled relative to longitudinal axis 13. For example, second end wall 32 can be moved toward and away from first end wall 26 of the adjacent plate segment. The plate segments can also be pivoted proximally and distally relative to the adjacent plate segment so that proximal surfaces 36 are not aligned linearly with one another along the plate assembly 12. The universal pivoting capability of the plate segments relative to one another about longitudinal axis 13 allows the plate assembly 12 to be adapted to the positioning of the anchor assembly locations in the patient. In addition, hole 18 is elongated in a direction paralleling longitudinal axis 13 to provide further adaptability in the positioning of plate assembly 12 relative to the anchor assembly locations.

Once the plate segments are in the desired positioned and orientation in the patient and positioned on mounting portions 54 of the anchor assemblies 50, engaging member 58 is secured to the anchor assembly 50 and against the corresponding plate segment to secure the connected plate segments to one another. In the embodiments of FIGS. 2-6, engaging member 58 engages proximal surface 36 of plate segment 14a and presses distal surface 38 against shoulder 56. Body 16 includes a longitudinal slot 20 extending from second end wall 32 and through side walls 30, 34 to a location adjacent to first end wall 26. Slot 20 divides body 16 into proximal and distal components that flex relative to one another about their connection adjacent first end wall 26, allowing the components of body 16 to be compressed to close socket 22 around ball member 24. The first and second components of body 16 grip ball member 24 to rigidly or semi-rigidly fix plate segments 14a and 14b to one another. Plate segment 14b can be similarly fixed to plate segment 14c.

Figure 7:
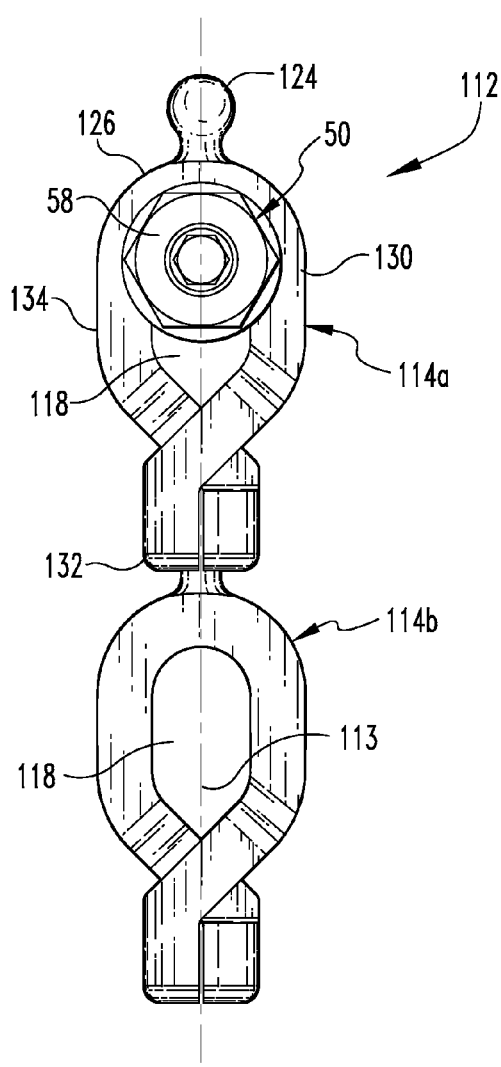
FIG. 7 is a plan view of another embodiment spinal stabilization system.
Figure 8:
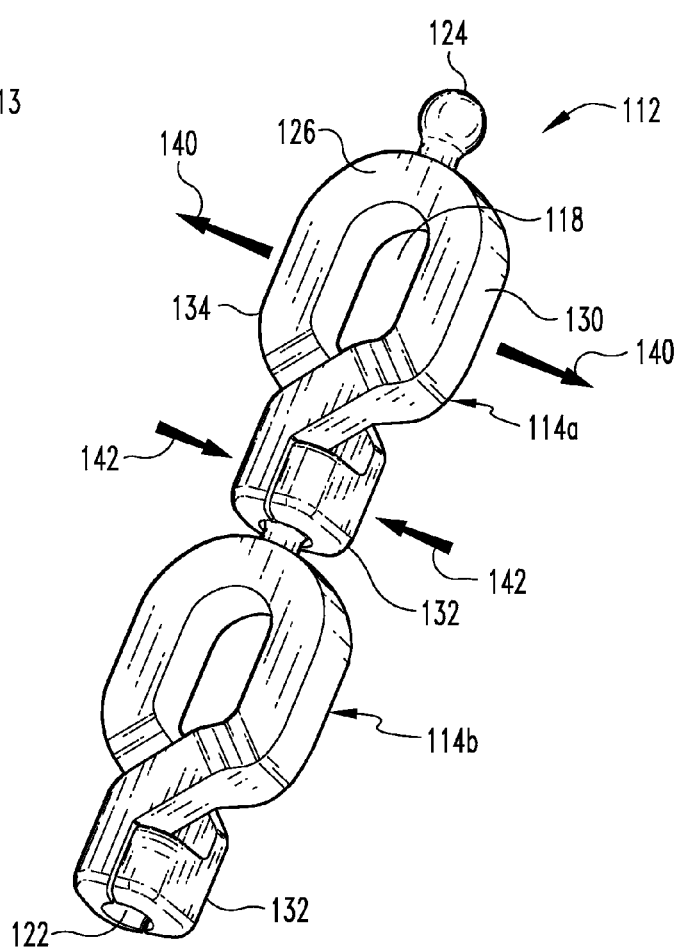
FIG. 8 is a perspective view of the spinal stabilization system of FIG. 7.
Figure 9:
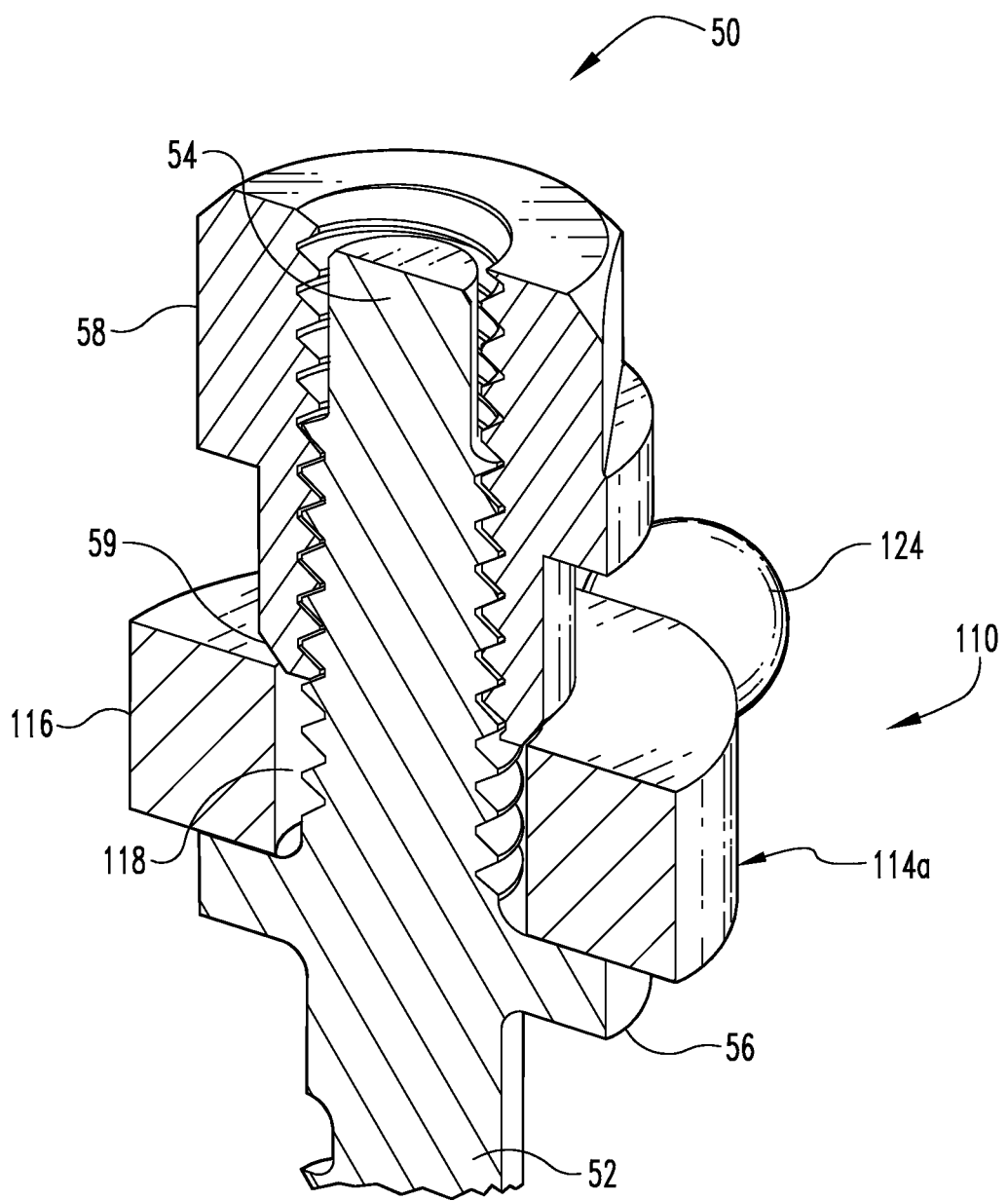
FIG. 9 is a longitudinal section along a bone anchor showing engagement of the anchor to a plate segment of the spinal stabilization system of FIG. 7.

FIGS. 7-9 show another embodiment plate assembly 112 with anchor assembly 50. Unless noted specifically herein, this embodiment can include any one or combination of the features of the other plate assemblies disclosed herein. In addition, plate assembly 12 can include any one or combination of features of the other plate assembly embodiments disclosed herein. Plate assembly 112 also includes multiple plate segments 114a, 114b pivotally coupled to one another on a longitudinal axis 113. In this embodiment, plate segments 114a, 114b and their respective holes 118 are centered on longitudinal axis 113. In addition, engaging member 58 of anchor assembly 50 is modified to expand hole 118 of the respective plate segment 114a, 114b to which it is engaged by laterally outwardly flexing portions of body 116 around hole 118 away from longitudinal axis 113. This in turn flexes the end of body 116 of plate segment 114a, 114b to reduce the size of socket 122 and grip ball member 124 of the adjacent plate segment received therein. Collapsing of socket 122 rigidly or semi-rigidly fixes adjacent plate segments to one another.

Body 116 includes a first end wall 126 from which first and second components of body 116 extend along opposite side walls 130, 134 to a second end 132. The first and second components body 116 extend along opposite sides of hole 118 and cross over one another and cross over longitudinal axis 113 at second end 132 to opposing sides of socket 122 at second end 132. Each end of the components forms a respective half of socket 122 on an opposite side of longitudinal axis 113. Accordingly, as shown in FIG. 9, as the distal end 59 of engaging member 58 is received in hole 118, the body components flex at first end wall 126 and around hole 118 to move laterally outwardly away from longitudinal axis 113, as indicated by arrows 140, which in turn moves the ends of the components defining socket 122 toward one another, as indicated by arrows 142, to clamp ball member 124 of the adjacent plate segment therein.

Figure 10:
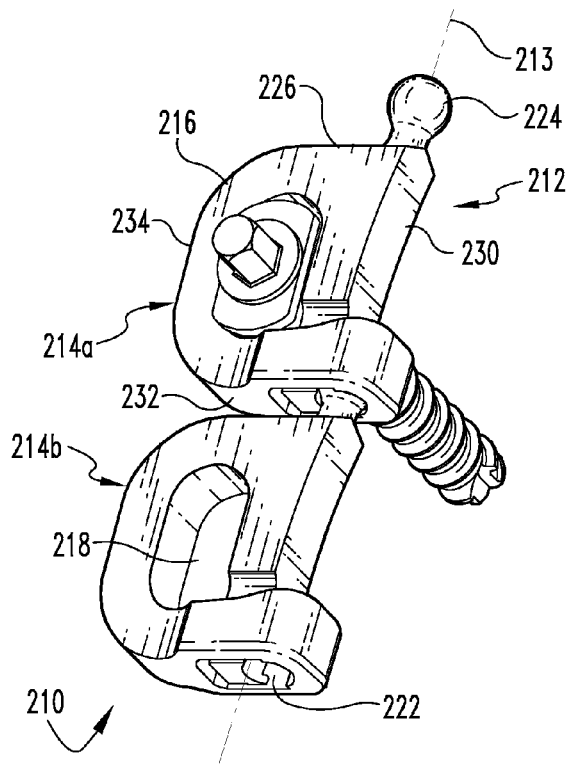
FIG. 10 is a perspective view of another embodiment spinal stabilization system.
Figure 11:
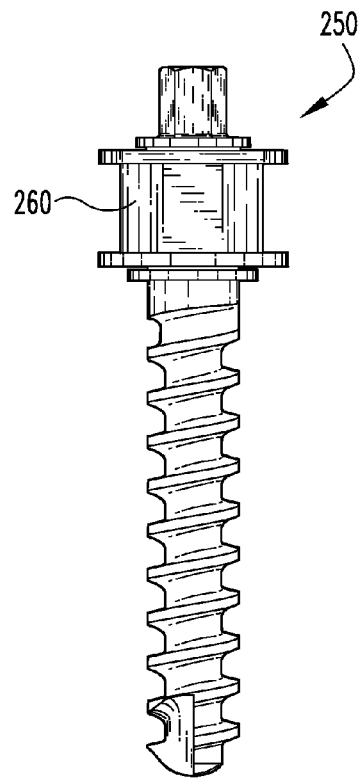
FIG. 11 is an elevation view of a bone anchor of the spinal stabilization system of FIG. 10.
Figure 12:
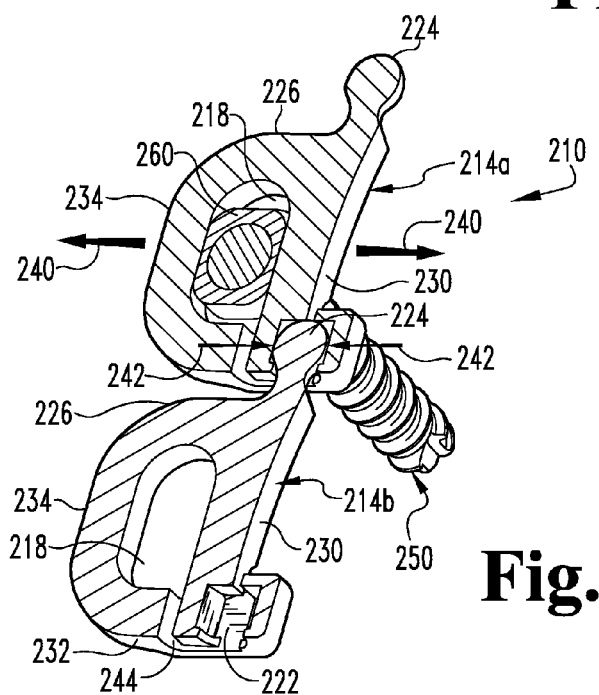
FIG. 12 is a perspective view in longitudinal section of the spinal stabilization system of FIG. 10.

FIGS. 10-12 show another embodiment stabilization system 210 that includes another embodiment plate assembly 212 and another embodiment anchor assembly 250. Unless noted specifically herein, this embodiment can include any of the features of the other plate assembly embodiments disclosed herein. Plate assembly 212 also includes multiple plate segments 214a, 214b pivotally coupled to one another on a longitudinal axis 213. In this embodiment, plate segments 214a, 214b and their respective holes 218 are offset laterally from longitudinal axis 213. Body 216 includes a first end wall 226 from which first and second components of body 216 extend along opposite side walls 230, 234 to a second end 232. At second end 232, the first component of body 216 along side wall 230 extends into a receptacle 244 formed by the second component of body 216 where is extends across side wall 234. In receptacle 244, each of the components defines a respective portion of socket 222 on opposite sides of longitudinal axis 213. Socket 222 receives ball member 224 of the adjacent plate segment. The portion of socket 222 defined by the component along side wall 230 is offset from longitudinal axis 213 toward second side wall 234, and the portion of socket 222 defined by the component along side wall 234 is offset from longitudinal axis 213 toward first side wall 230. Thus, the components cross over one another and longitudinal axis 213 to form opposing sides of socket 222 at second end 232.

Anchor assembly 250 is similar to anchor 150 discussed above, but includes a cam portion 260 that is received in hole 218. Cam portion 260 is rotated in hole 218 to engage and push apart the opposite components of body 216 along side walls 230, 234. This causes the body components to flex at first end wall 226 and move laterally outwardly away from longitudinal axis 213, as indicated by arrows 240, which in turn moves the ends of the components defining socket 222 toward one another, as indicated by arrows 242, to clamp ball member 224 of the adjacent plate segment therein.

In the illustrated embodiments, the bodies of the plate segments are shown to define an oval or D-shaped configuration. Other embodiments contemplate other configurations for the shapes of the plate segment bodies, such as square, rectangular, serpentine, polygonal, circular, and irregular shapes, for example. In addition, the plate segments can be elongated so that each plate segment spans one or more vertebral levels before its pivotal connection to an adjacent plate segment. The plate segments of a particular plate assembly need not be identical in size, shape or length to one another. In addition, a particular plate assembly can employ any combination of plate segments selected from any of the plate segment embodiments discussed herein.

It is contemplated that the plate segments can be comprised of a metal material, such as stainless steel, titanium, chrome-cobalt, and alloys and composites thereof. The plate segments may also be comprised of a polymer, such as, for example, polyetheretherketone (PEEK), polyetherketoneketone (PEKK), polymethylmethacrylate, polyurethane, silicone, silicone-polyurethane copolymers, epoxy, polycarbonate, polyketone, polyester, polyethylene, polyimide, polylactic acid, polypropylene, polystyrene, polysulfone, polyvinyl chloride, polyamide, poly(tetrafluoroethene), polyphthalamide, polybutylene and mixtures or combinations of thereof.

Although various embodiments have been described as having particular features and/or combinations of components, other embodiments are possible having a combination of any features and/or components from any of embodiments as discussed above. As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the terms "proximal" and "distal" refer to the direction closer to and away from, respectively, an operator (e.g., surgeon, physician, nurse, technician, etc.) who would insert the medical implant and/or instruments into the patient. For example, the portion of a medical instrument first inserted inside the patient's body would be the distal portion, while the opposite portion of the medical device (e.g., the portion of the medical device closest to the operator) would be the proximal portion.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. A spinal stabilization system, comprising:
   at least a first anchor defining a first longitudinal axis and engageable to a first vertebra and a second anchor engageable to a second vertebra, said first and second anchors each including a bone engaging portion and a mounting portion extending proximally from said bone engaging portion, each of said first and second anchors further including an engaging member;
   a first plate segment defining a second longitudinal axis perpendicular to the first longitudinal axis and including a body defining a hole extending therethrough for receiving said first anchor, said body further defining a socket defining a third longitudinal axis; and
   a second plate segment including a body defining a hole extending therethrough for receiving said second anchor, said body of said second plate segment including a member extending into said socket to pivotally connect said second plate segment to said first plate segment, wherein the second plate extends along the second longitudinal axis in a first orientation and is configured to rotate about the third longitudinal axis such that the second plate extends along a fourth longitudinal axis in a second orientation,
   wherein said engaging member of said first anchor is movable to manipulate said body of said first plate segment to collapse said socket around said member and lock said second plate segment in position relative to said first plate segment.

2. The system of claim 1, wherein said first plate segment and said second plate segment extend along a longitudinal axis that intersects a location where said second plate segment is pivotally coupled to said first plate segment, each of said first and second plate segments including first and second end walls extending transversely to said longitudinal axis and first and second side walls extending along said longitudinal axis, said end walls and said side walls extending around said hole of said respective plate segment.

3. The system of claim 2, wherein said holes of said first and second plate segments are laterally offset from one another on opposite sides of said longitudinal axis.

4. The system of claim 2, wherein at least said first plate segment includes a slot that extends longitudinally through said second end wall and through each of said first and second side walls to a location adjacent said first end wall, said slot dividing said body into a proximal component and a distal component that flex relative to one another about said first end wall to collapse said socket when said engaging member of said first anchor is moved to manipulate said first plate segment.

5. The system of claim 4, wherein said second end wall of said first plate segment extends from said longitudinal axis in a direction angled away from said first end wall of said second plate segment.

6. The system of claim 2, wherein said first plate segment includes a first component extending along said first side wall and a second component extending along said second side wall, said second component extending to an end thereof that defines a receptacle at said second end wall that receives an end of said first component therein, said ends of said first and second components defining respective first and second portions of said socket on opposite sides of said longitudinal axis so that as said engaging member is positioned in said hole said first and second components move laterally away from one another along said hole to displace said respective socket portions toward one another at said second end wall and collapse said socket around said member of said second plate segment.

7. The system of claim 2, wherein said holes of said first and second plate segments and said pivotal connection of said first and second plate segments are centered on said longitudinal axis when said first and second plate segments are in a non-pivoted orientation relative to one another.

8. The system of claim 7, wherein said first plate segment includes a first component extending along said first side wall and a second component extending along said second side wall, said first and second components extending to ends thereof that cross over one another and cross over said longitudinal axis at said second end wall, said ends of said first and second components defining a respective portion of said socket on opposite sides of said longitudinal axis so that as said engaging member is positioned in said hole, said first and second components move laterally away from one another along said hole to move said respective socket portions toward one another at said second end wall and collapse said socket around said member of said second plate segment.

9. The system of claim 1, wherein said first bone anchor includes a shoulder between said bone engaging portion and said mounting portion and said body of said first plate segment is clamped between said engaging member and said shoulder in order to collapse said socket.

10. The system of claim 1, wherein said distal bone engaging portions of said first and second bone anchors each include a threaded shaft and said proximal mounting portions each include an elongated cylindrical post positioned in said hole of said respective plate segment.

11. The system of claim 10, wherein said engaging member is a nut threadingly engaged to said cylindrical post of said proximal mounting portion.

12. The system of claim 10, wherein said engaging member is a cam in said hole of said respective plate segment that is rotatable relative to said bone engaging portion to contact said body of said respective plate segment collapse said socket.

13. A spinal stabilization system, comprising:
  at least a first anchor defining a first longitudinal axis and engageable to a first vertebra and a second anchor engageable to a second vertebra, said first and second anchors each including a bone engaging portion and a mounting portion extending proximally from said bone engaging portion, each of said first and second anchors further including an engaging member engageable to said mounting portion;
  a first plate segment defining a second longitudinal axis and including a body defining a hole extending therethrough for receiving said first anchor, said body including first and second components that flex relative to one another, said first and second components further each defining a respective portion of a socket defining a third longitudinal axis; and
  a second plate segment including a body defining a hole extending therethrough for receiving said second anchor, said body of said second plate segment including a member extending into said socket to pivotally connect said second plate segment to said first plate segment, wherein the second plate extends along the second longitudinal axis in a first orientation and is configured to rotate about the third longitudinal axis such that the second plate extends along a fourth longitudinal axis in a second orientation,
  wherein said engaging member of said first anchor is movable to contact said body of said first plate segment and flex said first and second components to clamp said portions of said socket against said member to lock said second plate segment in position relative to said first plate segment.

14. The system of claim 13, wherein said holes of said first and second plate segments are laterally offset from said longitudinal axis and said pivotal connection of said first and second plate segments is centered on said longitudinal axis.

15. The system of claim 13, wherein said first plate segment and said second plate segment extend along a longitudinal axis, each of said first and second plate segments including first and second end walls extending transversely to said longitudinal axis and first and second side walls extending along said longitudinal axis, said end walls and said side walls extending around said hole of said respective plate segment.

16. The system of claim 15, wherein at least said first plate segment includes a slot in communication with said hole of said first plate segment that extends longitudinally through said second end wall and through each of said first and second side walls to a location adjacent said first end wall, said slot dividing said body into a proximal component and a distal component that flex relative to one another about said first end wall to collapse said socket.

17. The system of claim 15, wherein said first plate segment includes a first component extending along said first side wall and a second component extending along said second side wall, said second component extending to an end defining a receptacle at said first end wall that receives an end of said first component therein, said ends of said first and second components defining a respective portion of said socket on opposite sides of said longitudinal axis so that as said engaging member is positioned in said hole of said first plate segment said first and second components move laterally away from one another along said hole to displace said respective socket portions toward one another at said second end wall and collapse said socket around said member of said second plate segment.

18. The system of claim 13, wherein said holes of said first and second plate segments and said pivotal connection of said first and second plate segments are centered on said longitudinal axis when said first and second plate segments are in a non-pivoted orientation relative to one another.

* * * * *